United States Patent
Govari et al.

(10) Patent No.: US 11,083,563 B2
(45) Date of Patent: Aug. 10, 2021

(54) LIGHTWEIGHT BREAST IMPLANT

(71) Applicant: Biosense Webster (Israel) Ltd., Yokneam (IL)

(72) Inventors: Assaf Govari, Haifa (IL); Yehuda Algawi, Binyamina (IL); Ilya Sitnitsky, Nahariya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 185 days.

(21) Appl. No.: 15/986,109

(22) Filed: May 22, 2018

(65) Prior Publication Data
US 2019/0358024 A1   Nov. 28, 2019

(51) Int. Cl.
*A61F 2/12*   (2006.01)
*C08G 77/04*   (2006.01)
*C08L 83/04*   (2006.01)

(52) U.S. Cl.
CPC ............ *A61F 2/12* (2013.01); *C08G 77/04* (2013.01); *C08L 83/04* (2013.01)

(58) Field of Classification Search
CPC ........................................................ A61F 2/12
See application file for complete search history.

(56) References Cited

U.S. PATENT DOCUMENTS

| | | | |
|---|---|---|---|
| 4,992,312 A * | 2/1991 | Frisch | A61L 27/18 427/230 |
| 5,658,330 A * | 8/1997 | Carlisle | A61F 2/0077 623/11.11 |
| 9,949,821 B2 | 4/2018 | Beeckler | |
| 2006/0235094 A1 * | 10/2006 | Habibi-Naini | B29C 44/3446 521/50 |
| 2009/0214652 A1 | 8/2009 | Hunter et al. | |
| 2010/0082102 A1 | 4/2010 | Govil et al. | |
| 2011/0270391 A1 | 11/2011 | Chitre et al. | |
| 2011/0309541 A1 | 12/2011 | Thompson et al. | |
| 2012/0077010 A1 | 3/2012 | Manesis et al. | |
| 2012/0130489 A1 | 5/2012 | Chernomorsky et al. | |
| 2013/0289529 A1 | 10/2013 | Caira et al. | |
| 2015/0327985 A1 | 11/2015 | Hristov et al. | |
| 2016/0369100 A1 | 12/2016 | Kihara et al. | |
| 2017/0348089 A1 | 12/2017 | Becker | |
| 2018/0064530 A1 | 3/2018 | Glicksman | |

FOREIGN PATENT DOCUMENTS

KR   20080028549 A   4/2008

OTHER PUBLICATIONS

EP19175719.4-1124—Extended European Search Report dated Oct. 10, 2019.

* cited by examiner

*Primary Examiner* — Monica A Huson
*Assistant Examiner* — Kelsey C Grace
(74) *Attorney, Agent, or Firm* — Eugene L. Szczecina, Jr.

(57) ABSTRACT

A method for producing an implant, the method includes providing a hollow biocompatible shell to be implanted in an organ of a patient. At least two filling materials are injected at one or more locations in the shell, such that a mixture of at least two of the filling materials is configured to produce gas bubbles within a bulk of the mixture. The gas bubbles are formed in the injected filling materials by heating the shell containing the mixture of the injected filling materials.

9 Claims, 2 Drawing Sheets

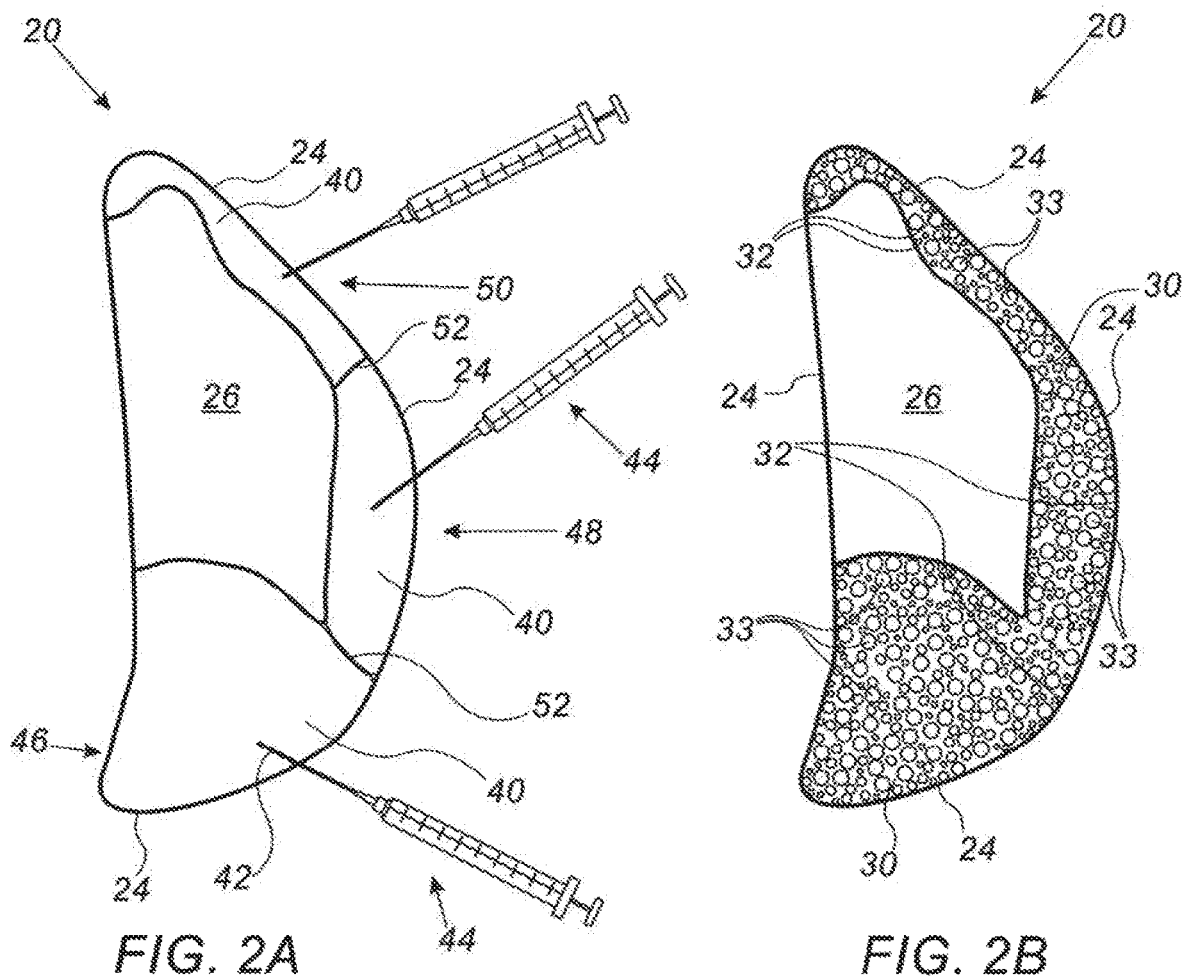
FIG. 2A
FIG. 2B
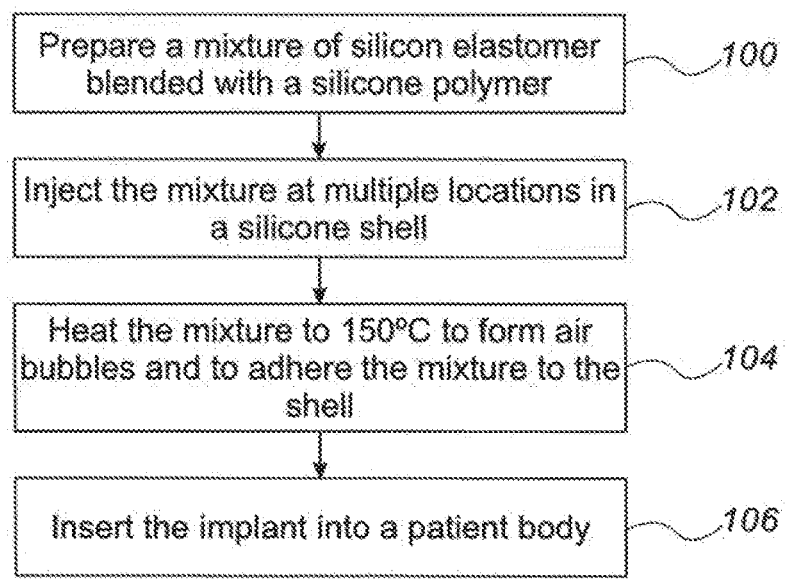
FIG. 3

LIGHTWEIGHT BREAST IMPLANT

FIELD OF THE INVENTION

The present invention relates generally to breast implants, and particularly to methods and devices for breast implants having reduced weight.

BACKGROUND OF THE INVENTION

Various types of implants, such as breast implants, are used in a variety of therapeutic and cosmetic applications.

For example, U.S. Patent Application Publication 2016/0369100 describes compositions for forming silicone elastomers thereby which have improved characteristics and which can be used for medical devices. The composition for forming a silicone elastomer can include (A) an organopolysiloxane having silicon-bonded alkenyl groups, (B) an organohydrogensiloxane having an average of two or more silicon-bonded hydrogen atoms in the molecule, (C) an inorganic filler, and (D) a filler treatment agent which includes an alkenyl-containing group.

U.S. Patent Application Publication 2011/0270391 describes an inflatable tissue expander or more permanent prosthesis, suitable for implantation in a breast. The tissue expander includes a puncturable, self-sealing anterior portion forming a fillable cavity, and posterior portion that is puncture resistant.

SUMMARY OF THE INVENTION

An embodiment of the present invention that is described herein provides a method for producing an implant, the method includes providing a hollow biocompatible shell to be implanted in an organ of a patient. At least two filling materials are injected at one or more locations in the shell, such that a mixture of at least two of the filling materials is configured to produce gas bubbles within a bulk of the mixture. The gas bubbles are formed in the injected filling materials by heating the shell containing the mixture of the injected filling materials.

In some embodiments, injecting the filling materials includes mixing the at least two of the filling materials to produce the mixture outside the shell, and injecting the produced mixture at the one or more locations in the shell. In other embodiments, injecting the at least two filing materials includes injecting each of the filling materials separately into the shell. In yet other embodiments, one of the at least two filling materials includes a silicone polymer.

In an embodiment, forming the gas bubbles includes heating the shell to a temperature above 100° C. In another embodiment, the method includes cementing the mixture to an inner surface of the shell by heating the shell.

In some embodiments, the mixture is at a liquid state prior to forming the gas bubbles, and heating the shell includes curing the mixture from the liquid state to a solid state. In other embodiments, injecting the at least two filing materials includes injecting a first volume of the at least two filling materials at a first location in the shell, and injecting a second different volume of the at least two filling materials at a second different location in the shell.

In an embodiment, the method includes injecting an additional filling material at an additional location in the shell, such that the mixture of the filling material covers at least part of an inner surface of the shell. In another embodiment, injecting the additional filling material includes injecting silicone gel.

There is additionally provided, in accordance with an embodiment of the present invention, an implant that includes a hollow biocompatible shell and at least two filling materials. The shell is configured to be implanted in an organ of a patient, and to contain the filling materials, and at least two of the filling materials are configured to mix with one another and to produce gas bubbles within a bulk of a mixture of the at least two of the filling materials.

The present invention will be more fully understood from the following detailed description of the embodiments thereof, taken together with the drawings in which:

BRIEF DESCRIPTION OF THE DRAWINGS

FIG. 2A is a schematic, pictorial illustration of filling material injected into a breast implant, in accordance with embodiments of the present invention;

FIG. 2B is a schematic, pictorial illustration of a breast implant, in accordance with embodiments of the present invention; and FIG. 3 is a flow chart that schematically illustrates a method for producing a breast implant, in accordance with an embodiment of the present invention.

DETAILED DESCRIPTION OF EMBODIMENTS

Overview

Figure 1:
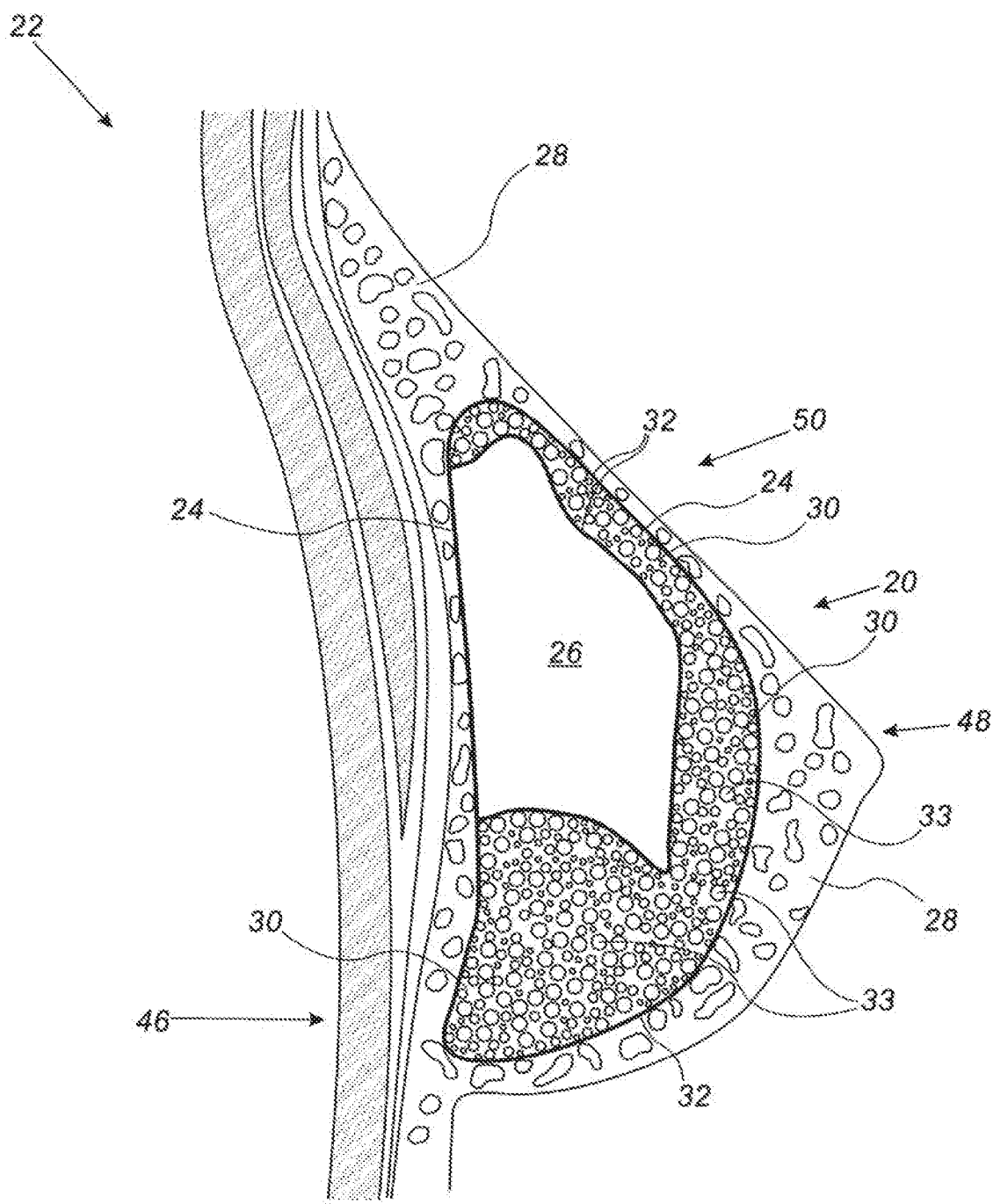
FIG. 1 is a schematic, pictorial illustration of breast implant implanted in a woman's breast, in accordance with embodiments of the present invention.

Medical implants, such as breast implants, are typically used for reconstructing a human breast after excision or for shaping the size and contour of breasts in cosmetic applications. A conventional breast implant is typically filled with some filling material, such as silicone gel that conforms to the texture of natural tissue of the breast. The implant further comprises a biocompatible shell adapted to encapsulate the filling material and to be implanted in the human breast so as to conform to the texture of the breast tissue.

A breast implant is desirably required to be lightweight and at the same time firm. A breast implant filled with a large amount of silicone gel, however, typically has excess weight, which may cause inconvenience and even medical problems such as back ache.

Embodiments of the present invention that are described hereinbelow provide a lightweight breast implant that conforms to the texture of natural tissue of the breast, as well as methods for producing this breast implant. In some embodiments, two or more filling materials, such as a silicon elastomer and one or more other types of silicone polymers, are injected into a hollow biocompatible shell to be implanted in a patient breast. The filling materials may be mixed together before being injected into the shell, or alternatively mixed within the shell.

The mixture produced from the filling materials is typically formed in a liquid state, e.g., emulsion, and is configured to produce gas bubbles within a bulk of the mixture, in response to heating the shell including the mixture.

In some embodiments, the mixture is heated to 150° C. and subsequently cooled to room temperature (e.g., 25° C.) in a curing process that induces the formation of the gas bubbles in the bulk of the filling material. The curing process and bubble formation are configured to shape the filling material in a form of a solid sponge having a smooth outer surface (i.e., without pores or having the pores closed). The curing process is further configured to cement the sponge to the inner surface of the biocompatible shell so as to produce the implant as a single firm unit.

In some embodiments, the implant may comprise filling materials additional to the mixture materials, such as silicone gel used in conventional implants, which is inserted into the shell and is later wrapped with the sponge-shaped filling material in accordance with the process described above.

Filling materials may be injected into the shell at one or more selected locations, so as to shape the contour of the implanted breasts and optimize the overall weight of the implant. For example, a breast implant may comprise a thick layer of filling material at the base of the implant, and a thinner layer of the same filling material at the front of the implant.

The disclosed techniques provide the implanted patient with a lightweight yet firm breast implant that conforms to the texture of natural tissue of the breast. Furthermore, the disclosed techniques provide a physician, such as a plastic surgeon, with a flexibility to optimize the weight of the implant without compromising the overall size, shape and texture of the implanted breast.

System Description

FIG. 1 is a schematic pictorial illustration of a breast implant 20 implanted in a woman's breast 22, in accordance with an embodiment of the present invention. Typically, implant 20 is a prosthesis used for shaping the size and contour of breast 22.

Breast 22 comprises natural tissue 28 surrounding implant 20. In some embodiments, implant 20 comprises a hollow biocompatible shell 24, made from silicone or any other suitable material, which is configured to encapsulate soft filling materials that resemble the texture of tissue 28.

In an example embodiment, shell 24 comprises gel 26, made from silicone or any other suitable material, and adapted to serve as filling material of implant 20.

In some embodiments, shell 24 comprises a porous material, referred to herein as a sponge 30, made from a mixture of two or more suitable materials. In example embodiments, the mixture of materials is produced by blending a silicone polymer, such as a silicone elastomer (e.g., Nusil Med 4805, Shore hardness A7) with another type of silicone polymer (e.g., Nusil Med 4-4800), both of these materials are provided, for example, by NuSil™ Technology LLC, 1050 Cindy Lane, Carpinteria, Calif. 93013.

In some embodiments, sponge 30 comprises gas bubbles 33 located in the bulk of the sponge. Sponge 30 comprises an outer surface 32, which has a smooth texture without any pores, in which the pores are closed.

In some embodiments, shell 24 is physically and chemically stable, so as to create a sustainable physical insulation between sponge 30 and tissue 28. Furthermore, sponge 30 and the inner surface of shell 24 are well cemented to one another. In other words, sponge 30 is configured to adhere to the inner surface of shell 24.

In some embodiments, the formation of gas bubbles 33, instead of the silicone gel, reduces the weight of implant 20, while still providing firm texture of sponge 30 so as to obtain the required shape and contour of breast 22.

In some embodiments, the portion and distribution of sponge 30 within implant 20 is controllable, as will be described in FIGS. 2A and 2B below. In the example of FIG. 1, sponge 30 is designed thicker at a base 46 (e.g., located at the lower part) of breast 22, compared to the thickness of sponge 30 at a front area 48 and at an upper area 50 of breast 22.

In the example of FIG. 1, gel 26 is inserted or injected into an inner section of the inner volume of shell 24, whereas filling material 40 is injected into an outer section of the inner volume of shell 24.

In another example, filling material 40 is injected into the inner section of shell 24, and gel 26 is injected at the outer section of shell 24, so that at least part of the inner surface of shell 24 is in direct contact with gel 24.

The configuration of implant 20 shown in FIG. 1 is an example configuration that is shown purely for the sake of conceptual clarity. In alternative embodiments, any other suitable configuration can be used. For example, implant 20 may comprise filling material solely made from sponge 30, without gel 26.

Furthermore, embodiments of the present invention are by no means limited to a specific geometry, types of filling materials, and number of interfaces within the fillings materials and between the filling materials and the shell.

Embodiments of the present invention are also not limited to this specific type of implant. The principles described herein may similarly be applied to other suitable types of medical and aesthetic implants.

FIG. 2A is a schematic, pictorial illustration of filling material 40 injected into breast implant 20, in accordance with embodiments of the present invention. In some embodiments, filling material 40 may comprise any suitable mixture of two or more materials, such as the silicone elastomer (which is a silicone polymer) and one or more other types of silicone polymers described in FIG. 1 above.

In some embodiments, the silicone elastomer and the other silicone polymers are mixed, before being injected into shell 24, using any suitable blending machine. The mixture forms filling material 40, which is later injected into implant 20. In alternative embodiments, at least two materials of filling material 40 are injected into implant 20 separately, and are mixed within the shell during a later process step of filling material 40, as will be described in FIG. 2B below.

In some embodiments, the materials comprising filling material 40 are injected into implant 20 using a syringe 44. In the example of FIG. 2A, the injection is carried out by puncturing a small hole in implant 20. In other embodiments, implant 20 may comprise one or more valves, so that the materials comprising filling material 40 are inserted into implant 20 using syringe 44 or any other suitable mechanism without puncturing shell 24.

The following embodiments describe the process steps of injecting filling material 40 into implant 20. These embodiments are also applicable for separately injecting at least two materials comprising filling material 40, using a sequence of two or more respective injection process steps, and for inserting these materials using any other suitable insertion method.

As described in FIG. 1 above, filling material 40 may be injected into implant 20 at one or more locations, whereas the amount of injected material may differ among the locations. In the example of FIG. 2A, filling material 40 is injected at three locations. The largest amount of filling material 40 is injected into base 46 of implant 20, a smaller amount is injected into front area 48 and the smallest amount is injected into upper area 50 of implant 20. The plurality of injections at respective locations may undesirably form separate chunks of filling material 40 coupled to one another at one or more interfaces 52. This issue is addressed further below.

In other embodiments, the injection may be carried out using any other suitable number of locations, and any suitable amount of filling material(s) injected at each location. Furthermore, the portion of gel 26 may vary between zero and any suitable percentage of the inner volume of implant 20. The portion of filling material 40 injected at each location and the volumetric ratio between gel 26 and filling material 40 determines the size, shape and weight of implant 20.

In some embodiments, filling material 40 may be injected at one or more locations of shell 24 and gel 26 may be inserted into shell 24 at a later stage of the production process as will be described in FIG. 2B and FIG. 3 below.

FIG. 2B is a schematic, pictorial illustration of breast implant 20, in accordance with an embodiment of the present invention. FIG. 2B depicts implant 20 after applying to the implant one or more thermal process steps subsequently to the process steps described in FIG. 2A above.

In some embodiments, implant 20 as described in FIG. 2A, is heated to a suitable temperature using a sequence of one or more thermal process steps, also referred to herein as a curing process. The thermal process steps may be carried out using any suitable sequence of heating and cooling cycles. In an example embodiment, the thermal process may comprise a single heating step, starting at room temperature (e.g., 25° C.) and heating up to an exemplary temperature of 150° C. In other embodiments, the maximal heating temperature of the thermal process may comprise any suitable temperature between 100° C. and 200° C.

In some embodiments, the curing process changes the matter phase of filling material 40 to sponge 30 by locally forming gas bubbles 33 trapped in the bulk of sponge 30. In an example embodiment, filling material 40 is heated to 150° C. and subsequently cooled to room temperature (25° C.). Such a thermal cycle transforms filling material 40 from a liquid state (e.g., emulsion) into a solid state.

During the formation of sponge 30 from filling material 40, the filling material may evaporate at specific locations, resulting in the formation of gas bubbles 33 that form the structure of sponge 30. Note that the gas bubbles produced during the curing process may contain byproducts of filling material 40, or air and/or other gases absorbed from the environment during various process steps of implant 20, or a combination thereof.

In some embodiments, the bubble size and the distribution of gas bubbles 33 in space may be determined by the sequence of the curing process, and by the composition and structure of the materials comprising filling material 40.

Note that bubbles 33 are formed solely in the bulk of sponge 30, whereas surface 32 of sponge 30 remains flat and smooth, e.g., without pores. The combination of high temperature (e.g., 150° C.) and smoothness of surface 32, enables cementing between surface 32 of sponge 30 and an inner surface of shell 24. In an embodiment, the curing process eliminates interfaces 52 by forming a contiguous bulk of sponge 30 distributed across implant 20 as shown in FIGS. 1 and 2B.

In alternative embodiments, at least two of the materials comprising filling material 40 are injected separately into implant 20 and the thermal process causes these materials to be mixed together into a mixture within the implant, for example by a thermal-driven diffusion process or using any other suitable thermal-related mechanism.

In some embodiments, gel 26, or any other suitable material instead of or in addition to gel 26, may be inserted into shell 24 after the formation of sponge 30. These embodiments allow using any suitable filling materials that cannot withstand high temperatures, such as 150° C. By injecting filling material 40 at selected locations of shell 24, sponge 30 is formed at these selected locations, and gel 26 and/or other materials may be injected into shell 24 thereafter so as to fill the desired volume of shell 24.

FIG. 3 is a flow chart that schematically illustrates a method for producing breast implant 20, in accordance with an embodiment of the present invention. The method begins with preparing filling material 40, which is a mixture of a silicone polymer, such as a silicone elastomer (e.g., Nusil Med 4805, Shore hardness A7 or A5) blended with another type of silicone polymer (e.g. Nusil Med 4-4800) at a materials blending step 100. Note that filling material 40 may be in the form of a liquid having high viscosity, such as an emulsion.

In some embodiments, the mixing process of step 100 may be carried out by a manufacturer, such as NuSil™ Technology LLC, and delivered as a mixture to the producer of implant 20. In another embodiment, at least two of the materials of filling material 40 are provided as separate materials, to be blended at step 100 by the manufacturer of implant 20.

At an injection step 102, the mixture of materials comprising filling material 40 is injected at one or more locations in shell 24. The injection may be carried out using syringe 44 or any other suitable device. As depicted in FIG. 2A above, different portions of filling material may be injected at different locations of implant 20. In alternative embodiments, at least two materials of filling material 40 are not mixed at step 100, and, at step 102, are injected separately into shell 24 using a sequence of two or more respective injection operations.

In some embodiments, shell 24 may contain, instead of or in addition to, silicone gel 26 any other suitable material, such as saline solutions. These materials may be inserted before or after performing step 102, so that the injection locations of filling material 40 are selected to obtain the desired shape and texture of breast 22. In the example of FIG. 2A, filling material 40 is injected as a buffering layer between gel 26 the outer-facing areas of shell 24, such as base 46, front area 48 and upper area 50. Note that filling material 40 may be injected at selected locations of shell 24, before inserting gel 26 into shell 24.

At a thermal processing step 104, implant 20 is heated from room temperature (e.g., 25° C.) to 150° C. or even a higher temperature and then cooled to room temperature. During the thermal process the emulsion of filling material 40 is transformed from liquid state into a solid state so as to form sponge 30.

During step 104, filling material 40 evaporates at specific locations having evaporation temperature lower than of the bulk of material 40. The local evaporations form across the bulk of material 40, gas bubbles 33 that define the structure of sponge 30. In some embodiments, thermal processing step 104 further results in cementing between surface 32 and the inner surface of shell 24.

In other embodiments, silicone gel 26 may be injected after the completion of processing step 104. The injection of gel 26 after thermal processing step 104 may prevent any heating-related damage to gel 26 associated with the thermal process. This sequence may allow using other filling materials that are susceptible to temperatures substantially higher than 37° C. (body temperature), such as 150° C. Furthermore, after step 104, other materials such as saline solution, may be injected instead of or in addition to gel 26. In some embodiments, step 104 concludes the production process of implant 20. Note that steps 100, 102 and 104 are depicted purely by way of example for the sake of simplicity and clarity. In other embodiments, each of these steps may comprise sub-steps. Moreover, the production process of implant 20 may comprise additional steps, such as a step of repairing the small holes punctured, at step 102, by needle 42 of syringe 44. The repairing of the holes may be carried out at one or more additional process steps, or at step 104.

At an implantation step 106, implant 20 is delivered to a physician, such as a plastic surgeon, who carries out the implantation procedure of implant 20 in breast 22. Step 106 terminates the method of FIG. 3.

Although the embodiments described herein mainly address breast implants, the methods and systems described herein can also be used in other applications, such as in any type of light weight implants.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for producing an implant, the method comprising:
providing a hollow biocompatible shell to be implanted in an organ of a patient;
injecting, at one or more locations in the shell, at least two filling materials, wherein a mixture of at least two of the filling materials is configured to produce gas bubbles within a bulk of the mixture; and
forming the gas bubbles in the injected filling materials by heating the shell containing the mixture of the injected filling materials,
wherein said filling materials comprise a silicone elastomer and a silicone polymer.

2. The method according to claim 1, wherein injecting the filling materials comprises mixing the at least two of the filling materials to produce the mixture outside the shell, and injecting the produced mixture at the one or more locations in the shell.

3. The method according to claim 1, wherein injecting the at least two filing materials comprises injecting each of the filling materials separately into the shell.

4. The method according to claim 1, wherein forming the gas bubbles comprises heating the shell to a temperature above 100° C.

5. The method according to claim 1, and comprising cementing the mixture to an inner surface of the shell by heating the shell.

6. The method according to claim 1, wherein the mixture is at a liquid state prior to forming the gas bubbles, and wherein heating the shell comprises curing the mixture from the liquid state to a solid state.

7. The method according to claim 1, wherein injecting the at least two filing materials comprises injecting a first volume of the at least two filling materials at a first location in the shell, and injecting a second different volume of the at least two filling materials at a second different location in the shell.

8. The method according to claim 1, and comprising injecting an additional filling material at an additional location in the shell, such that the mixture of the filling material covers at least part of an inner surface of the shell.

9. The method according to claim 8, wherein injecting the additional filling material comprises injecting silicone gel.

* * * * *